United States Patent
Li et al.

(10) Patent No.: US 11,180,501 B2
(45) Date of Patent: Nov. 23, 2021

(54) CRYSTAL FORM OF β-LACTAMASE INHIBITOR AND PREPARATION METHOD THEREFOR

(71) Applicant: QILU PHARMACEUTICAL CO., LTD., Shandong (CN)

(72) Inventors: Cheng Li, Shanghai (CN); Zhigang Huang, Shanghai (CN); Charles Z. Ding, Shanghai (CN); Weidong Li, Shanghai (CN)

(73) Assignee: QILU PHARMACEUTICAL CO., LTD., Shandong (CN)

( * ) Notice: Subject to any disclaimer, the term of this patent is extended or adjusted under 35 U.S.C. 154(b) by 0 days.

(21) Appl. No.: 16/767,372

(22) PCT Filed: Dec. 3, 2018

(86) PCT No.: PCT/CN2018/118864
§ 371 (c)(1),
(2) Date: May 27, 2020

(87) PCT Pub. No.: WO2019/105479
PCT Pub. Date: Jun. 6, 2019

(65) Prior Publication Data
US 2020/0385385 A1    Dec. 10, 2020

(30) Foreign Application Priority Data

Dec. 1, 2017    (CN) .......................... 201711251386.3

(51) Int. Cl.
C07D 471/08    (2006.01)

(52) U.S. Cl.
CPC ........ *C07D 471/08* (2013.01); *C07B 2200/13* (2013.01)

(58) Field of Classification Search
CPC .......................... C07D 471/08; C07B 2200/13
See application file for complete search history.

(56) References Cited

U.S. PATENT DOCUMENTS

| | | | |
|---|---|---|---|
| 2011/0046102 A1 | 2/2011 | Ledoussal et al. | |
| 2014/0288051 A1* | 9/2014 | Maiti ................. | A61K 31/5377 514/210.21 |
| 2014/0296526 A1 | 10/2014 | Patil et al. | |
| 2015/0141401 A1 | 5/2015 | Abe et al. | |
| 2015/0203503 A1 | 7/2015 | Patil et al. | |
| 2020/0010467 A1* | 1/2020 | Hu ....................... | A61K 31/439 |

FOREIGN PATENT DOCUMENTS

| | | |
|---|---|---|
| CN | 104768951 A | 7/2015 |
| EP | 2657234 A1 | 10/2013 |
| EP | 3466950 A1 | 4/2019 |
| WO | WO-2009091856 A2 | 7/2009 |
| WO | WO-2009133442 A1 | 11/2009 |
| WO | WO-2010126820 A2 | 11/2010 |
| WO | WO-2012086241 A1 | 6/2012 |
| WO | WO-2013030733 A1 | 3/2013 |
| WO | WO-2013030735 A1 | 3/2013 |
| WO | WO-2013149121 A1 | 10/2013 |
| WO | WO-2013149136 A1 | 10/2013 |
| WO | WO-2013180197 A1 | 12/2013 |
| WO | WO-2014091268 A1 | 6/2014 |
| WO | WO-2014135931 A1 | 9/2014 |
| WO | WO-2014141132 A1 | 9/2014 |
| WO | WO-2015063653 A1 | 5/2015 |
| WO | WO-2015110885 A1 | 7/2015 |
| WO | WO-2017206947 A1 | 12/2017 |

OTHER PUBLICATIONS

Mar. 12, 2019 International Search Report issued in International Patent Application No. PCT/CN2018/118864.
Mar. 12, 2019 Written Opinion of International Search Report issued in International Patent Application No. PCT/CN2018/118864.
CA Extended European Search Report regarding EP 18884744.6, dated Jul. 6, 2021.

* cited by examiner

*Primary Examiner* — Timothy R Rozof
(74) *Attorney, Agent, or Firm* — Harness, Dickey & Pierce, P.L.C.

(57) ABSTRACT

Disclosed in the present disclosure are a crystal form of a β-lactamase inhibitor and a preparation method therefor, as well as an application of the crystal form in preparing a β-lactamase inhibitor drug. (I)

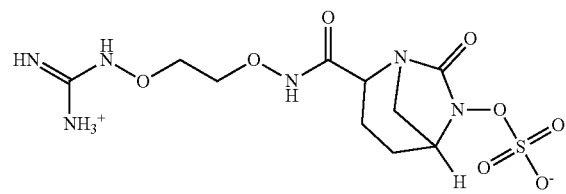

16 Claims, 3 Drawing Sheets

CRYSTAL FORM OF β-LACTAMASE INHIBITOR AND PREPARATION METHOD THEREFOR

CROSS-REFERENCE TO RELATED APPLICATIONS

This application is a 371 National Phase of International Application No. PCT/CN2018/118864, filed Dec. 3, 2018, which claims the benefit of Chinese Patent Application No. CN 201711251386.3, filed Dec. 1, 2017. The entire disclosures of the above applications are incorporated herein by reference.

FIELD OF THE INVENTION

The present disclosure relates to a novel class of β-lactamase inhibitors, specifically discloses a compound of formula (I) or a pharmaceutically acceptable salt thereof.

BACKGROUND OF THE INVENTION

There are several mechanisms by which bacteria develop resistance to β-lactam antibiotics, and one of the principal mechanisms is the production of enzymes that can hydrolyze the β-lactam ring and thus inactivate the antibiotics. Bacteria can also selectively alter the target of antibiotics. For example, methicillin-resistant Staphylococcus aureus has developed multiple resistance which is associated with the production of new $PBP_{2a}$, increased synthesis of PBPs, and decreased drug affinity. β-lactamase can rapidly bind to certain enzyme-resistant β-lactam antibiotics, allowing the drug to remain in the periplasmic space of the cytoplasmic membrane and fail to reach the target to exert an antibacterial effect. In addition, the outer membrane of G-bacteria is not easily permeable to certain β-lactam antibiotics, resulting in non-specific low-level resistance. There are also some active exocytosis systems on the cytoplasmic membrane of bacteria, by which bacteria actively release drugs to the exterior. Therefore, the combination of a β-lactam antibiotic and a β-lactamase inhibitor is the most clinically effective method. Bacteria can produce various types of β-lactamases, which can be classified into four classes: A, B, C, and D according to their amino acid and nucleotide sequences. Classes A, B, and D enzymes catalyze hydrolysis with serine as an active site, and class B enzymes cleave the ring by one or more metal atoms at the active site.

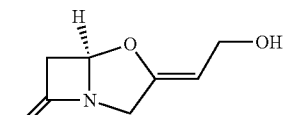

Clavulanic acid

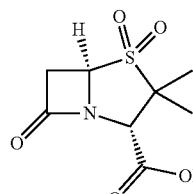

Sulbactam

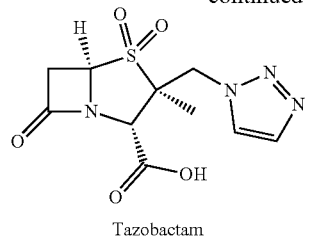

Tazobactam

The first well-known high-activity β-lactamase inhibitor is potassium clavulanate, and its combination with amoxicillin is still hot in the market to date. Two other important β-lactamase inhibitors on the market are sulbactam and tazobactam. These three drugs have a highly active β-lactam ring in their structures in common, which is the active site of these inhibitors. Although these three drugs are hot in the market, their antibacterial spectrum is very narrow. They are only effective on classes A and D β-lactamases, but are completely ineffective on class C enzymes and KPC enzymes which play an important role in class A enzymes.

In February 2015, FDA approved a new β-lactamase inhibitor named avibactam (NXL-104). This drug containing a novel diazabicyclo structure has a broader antibacterial spectrum than those three previous generation β-lactamase inhibitors described above. The patents for β-lactamase inhibitors including WO2009133442, WO2009091856, WO2010126820, WO2012086241, WO2013030733, WO2013030735, WO2013149121, WO2013149136, WO2013180197, WO20140191268, WO2014141132, WO2014135931, WO2015063653, WO2015110885 and US20140296526, have disclosed a large number of new diazabicyclo compounds, among which MK-7655 and OP-0595 are two new drugs that have entered the clinical trial stage. MK-7655 has entered Phase III clinical trial stage, and OP-0595 has entered Phase I clinical trial stage. OP-0595 has excellent in vitro activity and is owned by Roche Pharmaceuticals. Therefore, diazabicyclo inhibitors will be a new direction for the development of β-lactamase inhibitors.

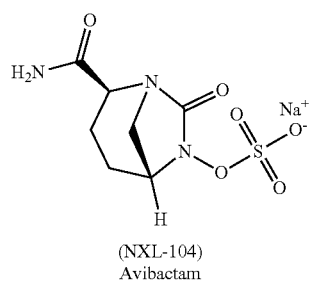

(NXL-104)
Avibactam

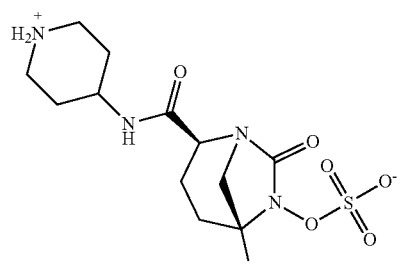

(MK-7655)

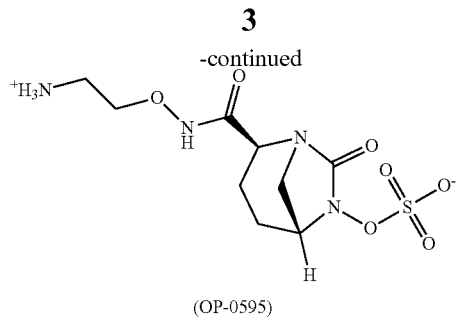

(OP-0595)

Content of the Invention

A crystal form A of the compound of formula (I), wherein the X-ray powder diffraction pattern thereof comprises characteristic diffraction peaks at the following angle 2θ: 16.053±0.2°, 16.53±0.2°, 22.782±0.2° and 25.742±0.2°.

(I)

A crystal form A of the compound of formula (I), wherein the X-ray powder diffraction pattern thereof comprises characteristic diffraction peaks at the following angle 2θ: 16.053±0.2°, 16.53±0.2°, 18.501±0.2°, 21.302±0.2°, 21.778±0.2°, 22.782±0.2°, 25.742±0.2° and 27.833±0.2°.

In some embodiments of the present disclosure, the XRPD pattern of the crystal form A is as shown in FIG. 1.

In some embodiments of the present disclosure, the analytical data of the XRPD pattern of the crystal form A is as shown in Table 1.

TABLE 1

| No. | 2θ Angle (°) | d-spacing (Å) | Intensity |
|---|---|---|---|
| 1 | 8.989 | 9.8297 | 387 |
| 2 | 14.363 | 6.1618 | 143 |
| 3 | 16.053 | 5.5164 | 1532 |
| 4 | 16.53 | 5.3584 | 1785 |
| 5 | 17.828 | 4.9712 | 151 |
| 6 | 18.121 | 4.8914 | 489 |
| 7 | 18.501 | 4.7918 | 625 |
| 8 | 20.177 | 4.3973 | 1185 |
| 9 | 21.302 | 4.1676 | 1199 |
| 10 | 21.778 | 4.0776 | 1255 |
| 11 | 22.782 | 3.9001 | 1582 |
| 12 | 23.889 | 3.7219 | 101 |
| 13 | 24.536 | 3.6251 | 462 |
| 14 | 25.212 | 3.5294 | 384 |
| 15 | 25.742 | 3.458 | 2124 |
| 16 | 27.833 | 3.2028 | 1026 |
| 17 | 28.323 | 3.1485 | 134 |
| 18 | 28.997 | 3.0768 | 373 |
| 19 | 29.366 | 3.0389 | 409 |
| 20 | 29.829 | 2.9928 | 108 |
| 21 | 30.632 | 2.9161 | 285 |
| 22 | 31.388 | 2.8477 | 112 |
| 23 | 32.351 | 2.7651 | 439 |
| 24 | 32.989 | 2.713 | 112 |
| 25 | 33.334 | 2.6857 | 166 |

TABLE 1-continued

| No. | 2θ Angle (°) | d-spacing (Å) | Intensity |
|---|---|---|---|
| 26 | 33.693 | 2.6579 | 130 |
| 27 | 34.575 | 2.5921 | 54 |
| 28 | 35.072 | 2.5565 | 130 |
| 29 | 35.408 | 2.533 | 177 |
| 30 | 36.287 | 2.4736 | 50 |
| 31 | 37.045 | 2.4247 | 66 |
| 32 | 37.539 | 2.3939 | 91 |
| 33 | 38.562 | 2.3328 | 91 |
| 34 | 38.981 | 2.3086 | 47 |

In some embodiments of the present disclosure, the differential scanning calorimetry curve of the crystal form A has an exothermic peak at 221.11±3° C.

In some embodiments of the present disclosure, the DSC pattern of the crystal form A is as shown in FIG. 2.

It can be seen from the DSC pattern that there is an exothermic peak near 221.11° C.

In some embodiments of the present disclosure, the thermogravimetric analysis curve of the crystal form A has a weight loss of 0.5689% occurred at 194.61±3° C.

The TGA pattern shows that the crystal form A has a weight loss of 0.5689% when heated to 194.61° C., and a large weight loss begins to occur after being heated to 200° C. The crystal form A does not contain water of crystallization or solvent of crystallization, and has good thermal stability.

The DVS pattern thereof is as shown in FIG. 4. The results show that the crystal form A has a hygroscopic weight gain of 0.2910% at 25° C./80% RH, showing that the crystal form A has a low hygroscopicity.

The present disclosure also provides a method for preparing a crystal form A of the compound of formula (I), comprising:

(a) adding the compound of formula (I) to a solvent and heating to 55-60° C. until it is completely dissolved;
(b) slowly cooling to 0° C. under stirring;
(c) stirring for 10-16 hours for crystallization;
(d) filtering, and drying by suction;
wherein, the solvent is pure water.

The present disclosure also provides a use of the crystal form A as described above or the crystal form prepared by the method as described above in the manufacture of a β-lactamase inhibitor for treating bacterial infection.

Technical Effect

The present disclosure is mainly characterized by the introduction of a completely novel side chain of a guanidinoxy group on the diazabicyclic ring. Compared with an amino group, the guanidinoxy group has more hydrogen-bonding sites, thereby providing better physicochemical properties such as water solubility. On the other hand, the guanidinoxy group has a pKa of 8.83, which is close to the pKa of an amino group (such as the terminal amino group at the side chain of lysine with a pKa of 8.95), and is much smaller than the pKa of a conventional guanidino group (such as that of arginine with a pKa of 12.48), therefore, the compound can maintain the same chemical stability as OP-0595. The experimental data of in vivo and in vitro activity of the compound provided in the present disclosure also show that the compound of formula (I) has an advantage over OP-0595 on activity. The crystal form described in the present disclosure has technical advantages such as easy preparation, good stability, and is less prone to polymorphic transformation, and is beneficial to the later production and application of drugs.

Definitions and Explanations

Unless otherwise indicated, the following terms and phrases used in this document are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The intermediate compounds of the present disclosure can be prepared by various synthetic methods known to those skilled in the art, including the embodiments described below, the embodiments formed by combining the embodiments described below with other chemical synthesis methods, and equivalent alternatives well-known for those skilled in the art. Preferred embodiments include, but are not limited to, the embodiments of the present disclosure.

The chemical reactions of the embodiments of the present disclosure are carried out in a suitable solvent, and the solvent should be suitable for the chemical change, and the reagents and materials required therefor of the present disclosure. In order to obtain the compounds of the present disclosure, it is sometimes necessary for those skilled in the art to modify or select the synthetic steps or reaction schemes based on the existing embodiments.

The present invention will be specifically described below by way of embodiments, but the scope of the present invention is not limited thereto.

All solvents used in the present disclosure are commercially available and can be directly used without further purification.

The present disclosure employs the following abbreviations: MW represents microwave; r.t. represents room temperature; aq represents aqueous solution; DCM represents dichloromethane; THF represents tetrahydrofuran; DMSO represents dimethyl sulfoxide; NMP represents N-methylpyrrolidone; EtOAc represents ethyl acetate; EtOH represents ethanol; MeOH represents methanol; dioxane represents 1,4-dioxane; HOAc represents acetic acid; Boc represents t-butoxycarbonyl, Cbz represents benzyloxycarbonyl, both of which are amino protecting groups; $Boc_2O$ represents di-tert-butyl bicarbonate; DIPEA represents diisopropylethylamine; TEA or $Et_3N$ represents triethylamine; $BnNH_2$ represents benzylamine; $PMBNH_2$ represents p-methoxybenzylamine; KOAc represents potassium acetate; NaOAc represents sodium acetate; $Cs_2CO_3$ represents cesium carbonate; $K_2CO_3$ represents potassium carbonate; $NaHCO_3$ represents sodium bicarbonate; $Na_2SO_4$ represents sodium sulfate; pyridine represents pyridine; NaOH represents sodium hydroxide; TEA or $Et_3N$ represents triethylamine; NaH represents sodium hydride; LiHMDS represents lithium bis(trimethylsilyl)amide; i-PrMgBr represents isopropylmagnesium bromide; t-BuOK represents potassium t-butoxide; t-BuONa represents sodium t-butoxide; $Pd_2(dba)_3$ represents tris(dibenzylideneacetone)dipalladium; $Pd(PPh_3)_4$ represents triphenylphosphine palladium; $Pd(dppf)Cl_2CH_2Cl_2$ represents [1,1'-bis(diphenylphosphino)ferrocene]palladium dichloride.dichloromethane; $Pd(OAc)_2$ represents palladium acetate; $Pd(PPh_3)_2Cl_2$ represents bis(triphenylphosphine)palladium dichloride; $Pd(PPh_3)_3Cl$ represents tris(triphenylphosphine) rhodium chloride; $Pd(OH)_2$ represents palladium hydroxide; Xantphos represents 4,5-bis(diphenylphosphine)-9,9-dimethylxanthene; Xphos represents 2-dicyclohexylphospho-2',4',6'-triisopropylbiphenyl; BINAP represents (±)-2,2'-bis-(diphenylphosphino)-1,1'-binaphthalene; Xantphos represents 4,5-bis-(diphenylphosphino)-9,9-dimethylxanthene; Xphos-Pd-G1 represents chloro(2-dicyclohexylphosphino-2',4',6'-triisopropyl-1,1'-biphenyl)[2-(2-aminoethyl)phenyl)]palladium(II); Xphos-PD-G2 represents chloro(2-dicyclohexylphosphino-2',4',6'-triisopropyl-1,1'-biphenyl)[2-(2'-amino-1,1'-biphenyl)]palladium(II); Xphos-Pd-G3 represents methanesulfonate(2-dicyclohexylphosphino-2',4',6'-triisopropyl-1,1'-biphenyl)[2-(2'-amino-1,1'-biphenyl)]palladium(II); $I_2$ represents iodine; LiCl represents lithium chloride; HCl represents hydrochloric acid; maleic acid represents maleic acid.

Compounds are named manually or by ChemDraw® software, and the commercially available compounds use their vendor directory names.

The Instrument and Analysis Method of the Present Disclosure:

1.1 X-Ray Powder Diffractometer (XRPD)

Instrument model: Bruker D8 advance X-ray diffractometer

Detection method: about 10-20 mg of the sample was used for XRPD detection.

The detailed XRPD parameters were as follows:

X-ray tube: Cu, kα, ($\lambda$=1.54056 Å).

X-ray tube voltage: 40 kV, X-ray tube current: 40 mA

Divergence slit: 0.60 mm

Detector slit: 10.50 mm

Anti-scattering slit: 7.10 mm

Scanning range: 4-40 deg

Step size: 0.02 deg

Step time: 0.12 seconds

Rotation speed of sample tray: 15 rpm 1.2 Differential Scanning Calorimeter (DSC)

Instrument Model: TA Q2000 differential scanning calorimeter

Detection method: samples (about 1 mg) were placed in a DSC aluminum crucible for detection, and heated from 30° C. to 300° C. with a heating rate of 10° C./min under the condition of 50 mL/min $N_2$.

1.3 Thermal Gravimetric Analyzer (TGA)

Instrument Model: TA Q5000 thermal gravimetric analyzer

Detection method: samples (2 mg to 5 mg) were placed in a TGA platinum crucible for detection, and heated from room temperature to 210° C. with a heating rate of 10° C./min under the condition of 25 mL/min $N_2$.

1.4 Dynamic Vapor Sorption (DVS)

Instrument model: SMS DVS Advantage dynamic vapor sorption analyzer

Detection conditions: samples (10 mg to 15 mg) were placed in a DVS sample tray for detection.

The detailed DVS parameters are as follows:

Temperature: 25° C.

Equilibrium: dm/dt=0.01%/min (shortest: 10 min, longest: 180 min)

Drying: 120 minutes at 0% RH

RH (%) gradient for testing: 10%

RH (%) gradient range for testing: 0%-90%-0%

The hygroscopicity was evaluated using the following scales:

| Scales for hygroscopicity | Hygroscopic weight gain* |
|---|---|
| Deliquescence | Absorbing sufficient water to form liquid |
| High hygroscopicity | ΔW % ≥ 15% |
| Medium hygroscopicity | 15% > ΔW % ≥ 2% |
| Low hygroscopicity | 2% > ΔW % ≥ 0.2% |
| No or almost no hygroscopicity | ΔW % < 0.2% |

*Hygroscopic weight gain at 25 ± 1° C. and 80 ± 2% RH

DETAILED DESCRIPTION OF THE PREFERRED EMBODIMENT

Figure 1:
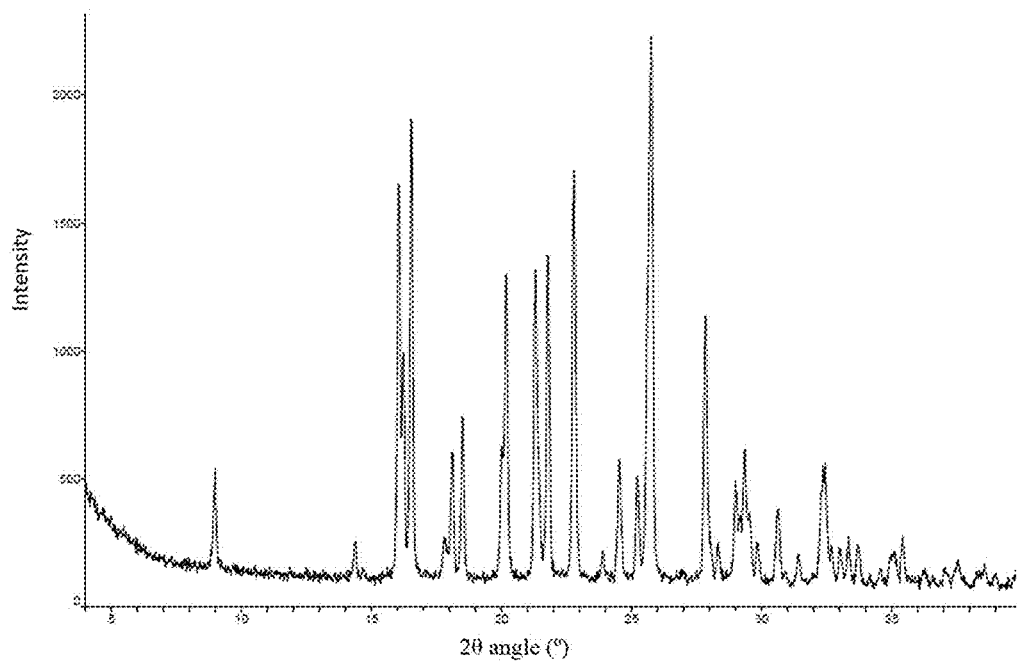
FIG. 1 is the XRPD pattern measured by Cu-Kα radiation of the crystal form A of the compound of formula (I).

In order to better understand the content of the present disclosure, the following embodiments further illustrate the present disclosure, but the present disclosure is not limited thereto.

Embodiment 1: Synthesis of the Compound of Formula (I)

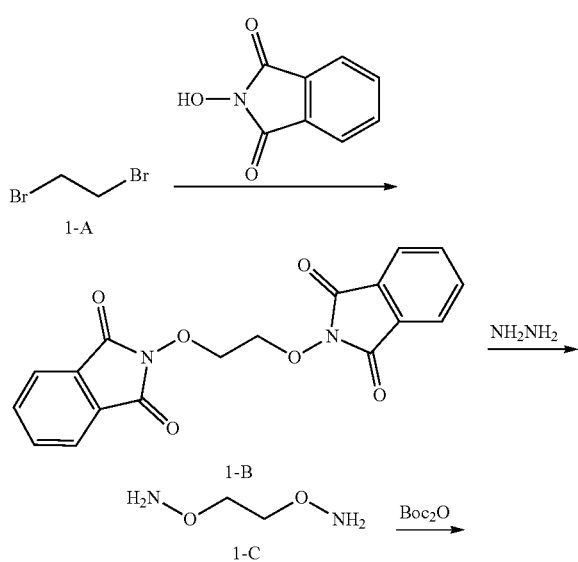

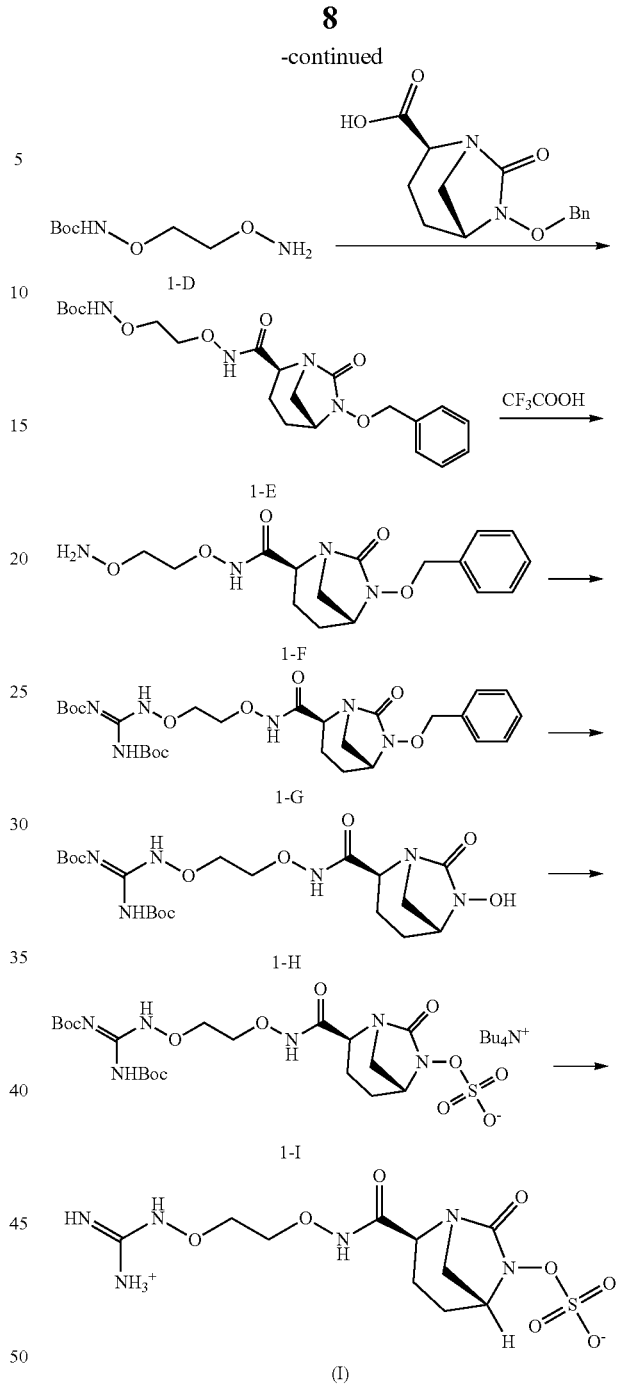

Step 1:

Starting material 1-A (50 g, 26.62 mmol), N-hydroxyphthalimide (8.69 g, 53.24 mmol) and triethylamine (6.73 g, 66.55 mmol) were dissolved in 100 mL N,N-dimethylformamide. The reaction solution was heated to 50° C. and stirred for 16 hours. The reaction solution was cooled to room temperature, poured into 100 mL ice-water under stirring, and filtered by suction. The obtained solid was washed with 10 mL cold water for three times, and dried to obtain compound 1-B.

Step 2:

The compound 1-B (6.0 g, 17.03 mmol) was suspended in 400 mL of dichloromethane and 150 mL of methanol, and 85% hydrazine hydrate (1.71 g, 34.06 mmol, 1.66 mL) was added thereto. The reaction solution was stirred at 25° C. for 18 hours, and filtered. The obtained filter cake was washed with 50 mL of ethyl acetate, and the filtrate was concentrated to dryness. The obtained residue was slurried with 40 mL of petroleum ether/ethyl acetate (3:1), then filtered and further slurried twice. The obtained filtrates were combined and concentrated to give compound 1-C.

Step 3:

The compound 1-C (980 mg, 10.64 mmol) was dissolved in 50 mL of dichloromethane and cooled to −10° C., then triethylamine (1.08 g, 10.64 mmol, 1.47 mL) was added by syringe, followed by dropwise addition of a solution of di-tert-butyl dicarbonate (2.32 g, 10.64 mmol) in 30 mL of dichloromethane. The reaction solution was slowly warmed to room temperature (25° C.) and stirred for 20 hours. After concentration, the residue was purified by silica gel column (ethyl acetate/petroleum ether mixture, gradient was 30%-50%) to obtain compound 1-D.

Step 4:

The compound 1-D (300 mg, 1.56 mmol), (2S,5R)-6-benzyloxy-7-oxy-1,6-diazabicyclo[3.2.1]oct-2-carboxylic acid (431.23 mg, 1.56 mmol) (the synthesis method refers to patent WO2012172368A1), EDCI (388.77 mg, 2.03 mmol), HOBt (274.02 mg, 2.03 mmol) and diisopropylethylamine (201.62 mg, 1.56 mmol, 272.46 μL) were sequentially added to 20 mL of dichloromethane. The reaction solution was stirred at room temperature (25° C.) for 20 hours, diluted with 30 mL dichloromethane, washed twice with 15 mL of water and once with 15 mL of brine. The organic phase was dried over anhydrous sodium sulfate and filtered. The filtrate was concentrated to dryness. The obtained crude product was purified by a silica gel column (ethyl acetate/petroleum ether mixture, gradient was 30%-50%) to obtain compound 1-E.

Step 5:

The compound 1-E (760.00 mg, 1.69 mmol) was dissolved in dichloromethane (7.00 mL), followed by addition of trifluoroacetic acid (3.08 g, 27.01 mmol, 2.00 mL) at 20° C. The reaction mixture was stirred for 3 hours, concentrated, diluted with ethyl acetate (50 mL), washed with saturated sodium bicarbonate (50 mL), and washed once with saturated brine (50 mL). The obtained organic phase was dried over anhydrous sodium sulfate, filtered and concentrated to give compound 1-F.

Step 6:

The compound 1-F (200.00 mg, 570.83 mol) and (E)-tert-butyl (tert-butoxycarbonyl)amino(methylene)carbamate (177.16 mg, 570.83 μmol) were dissolved in acetonitrile (2 mL). The reaction solution was stirred at 20° C. for 16 hours. After the reaction was completed, the reaction solution was concentrated. The obtained residue was subjected to silica gel column chromatography (ethyl acetate/petroleum ether=0-2/1 gradient elution) to obtain compound 1-G.

Step 7:

The compound 1-G (300.00 mg, 506.21 μmol) was dissolved in isopropanol (3.00 mL)/water (3.00 mL), followed by addition of wet palladium-carbon (50.00 mg, 10%). The mixture was stirred at 18-28° C. for 2 hours under hydrogen atmosphere, and filtered to obtain a solution of compound 1-H in isopropanol/water, which was directly used in the next reaction.

Step 8:

Sulfur trioxide trimethylamine complex (69.24 mg, 497.49 μmol) and triethylamine (10.07 mg, 99.50 μmol, 13.79 μL) were added to a solution of compound 1-H (250.00 mg, 497.49 μmol) in isopropanol (3.00 mL)/water (3.00 mL). The obtained mixture was stirred at 18-28° C. for 16 hours. After the reaction was completed, the reaction solution was washed with ethyl acetate/petroleum ether (2/1, 6 mL, twice). The aqueous phase was collected, and tetrabutylammonium hydrogenسulfate (168.43 mg, 496.07 μmol) was added. The obtained mixture was stirred at room temperature for 0.5 hour, and extracted with ethyl acetate (15 mL, twice). The obtained extract was washed with saturated brine (10 mL), dried over anhydrous sodium sulfate, filtered, and concentrated to obtain compound 1-I.

Step 9:

The compound 1-I (200.00 mg, 242.71 μmol) was dissolved in anhydrous dichloromethane (2.00 mL), the solution was cooled to 0° C. under nitrogen atmosphere, trifluoroacetic acid (1.54 g, 13.51 mmol, 1.00 mL) was added and the resulting mixture was stirred for 2 hours, then stirred at 25° C. for another 4 hours. Then the reaction solution was concentrated under atmosphere. The obtained residue was slurried for three times with acetonitrile (2 mL) to obtain a crude product, which was purified by high performance liquid chromatography to obtain the compound of formula (I).

$^1$H NMR (400 MHz, D$_2$O) 4.15 (s, 1H), 4.10-4.08 (m, 2H), 4.03-3.99 (m, 3H), 3.26 (d, J=12 Hz, 1H), 3.09 (d, J=12 Hz, 1H), 2.13-1.99 (m, 2H), 1.94-1.74 (m, 2H); LCMS (ESI) m/z: 383.1 (M+1).

Embodiment 2: Preparation of Crystal Form A of the Compound of Formula (I)

1.4 kg of the compound of formula (I) in 7 L of pure water was heated to 55-60° C., after complete dissolution, the solution was slowly cooled to 0° C. under stirring, and stirred for 12 hours for crystallization. The mixture was filtered, and dried by suction to obtain the crystal form A of the compound of formula (I).

Embodiment 3: Study on Hygroscopicity of the Crystal Form A of the Compound of Formula (I)

Experimental material: the crystal form A of the compound of formula (I)

Experimental Method: a sample (10-15 mg) was placed in a DVS sample tray for testing, and analyzed by dynamic vapor sorption (DVS) method.

Experimental result: hygroscopic weight gain ΔW=0.2910%

Experimental conclusion: the crystal form A of the compound of formula (I) has low hygroscopicity, and XPRD shows that the crystal form has not changed.

Embodiment 4: Study on Polymorphism of the Compound of Formula (I)

Experimental material: the compound of formula (I)

Experimental Method:

1. Three samples of about 35 mg of the compound of formula (I) were weighed and placed into 1.5 mL borosilicate glass bottles, respectively, followed by addition of 200 μL of solvent (see Table 2 for the solvent scheme). The obtained mixture was mixed evenly with ultrasound and then placed on a thermostatic oscillator, stirred at 40° C. in the dark for 2 days, and centrifuged quickly. The obtained solid was subjected to XRPD detection (wet product), and then dried in a vacuum dryer at 30° C. for about 15 hours. The obtained dry product was subjected to XPRD detection (dry product).

TABLE 2

Solvent scheme 1 for the study on polymorphism of the compound of formula (I)

| No. | Solvent | Condition | Crystal form |
|---|---|---|---|
| 1 | Methanol | Suspension | Crystal form A |
| 2 | Ethanol | Suspension | Crystal form A |
| 3 | Acetonitrile | Suspension | Crystal form A |
| 4 | Acetone | Suspension | Crystal form A |
| 5 | Ethyl acetate | Suspension | Crystal form A |
| 6 | Tetrahydrofuran | Suspension | Crystal form A |
| 7 | Cyclohexane | Suspension | Crystal form A |
| 8 | Water | Suspension | Crystal form A |
| 9 | Methanol-water (volume ratio 1:1) | Suspension | Crystal form A |
| 10 | Methanol-water (volume ratio 3:1) | Suspension | Crystal form A |
| 11 | Ethanol-water (volume ratio 1:1) | Suspension | Crystal form A |
| 12 | Ethanol-water (volume ratio 3:1) | Suspension | Crystal form A |
| 13 | Isopropanol-water (volume ratio 1:1) | Suspension | Crystal form A |

2. Three samples of about 35 mg of compound of formula (I) were weighed and placed into 1.5 mL borosilicate glass bottles, respectively, followed by addition of 600 μL of a solvent (see Table 3 for the solvent scheme). The obtained mixture was mixed evenly with ultrasound and then placed on a thermostatic oscillator, stirred at 40° C. in the dark for 2 days. Then the samples was placed into a fume hood and evaporated to dryness. The obtained samples were subjected to XRPD detection (wet product). The samples were placed in a vacuum dryer and dried at 30° C. for about 15 hours. The obtained dried samples were subjected to XRPD detection (dry product).

TABLE 3

Solvent Scheme 2 for the study on polymorphism of the compound of formula (I)

| No. | Solvent | Condition | Crystal form |
|---|---|---|---|
| 1 | Acetone-water (volume ratio 1:2) | Dissolved | Crystal form A |
| 2 | Acetonitrile-water (volume ratio 1:1) | Dissolved | Crystal form A |

Experimental results: see Table 2 and Table 3.

Experimental conclusion: No new crystal form has been observed after suspension and evaporation, and the crystal form A of the compound of formula (I) is stable.

Embodiment 5: Solubility Test of the Crystal Form A of the Compound of Formula (I)

Experimental material: the crystal form A of the compound of formula (I)

Experimental Method: about 2.0 mg sample was weighed and placed into a 1.5 mL borosilicate glass bottle, followed by addition of the following solvents with a pipetting gun respectively, and appropriate ultrasonic treatment was performed for dissolving. The test was carried out at room temperature, and the dissolution was detected by naked eye.

Experimental results: see Table 5.

Experimental conclusion: the crystal form A of the compound of formula (I) has a low solubility in various organic solvents, and has a certain solubility in water and alcohol solvents.

TABLE 4

Solvent scheme for the solubility test of the crystal form A of the compound of formula (I)

| No. | Solvent |
|---|---|
| 1 | Methanol |
| 2 | Ethanol |
| 3 | Isopropanol |
| 4 | n-Butanol |
| 5 | Acetonitrile |
| 6 | Acetone |
| 7 | Butanone |
| 8 | Methyl isobutyl ketone |
| 9 | Ethyl acetate |
| 10 | Isopropyl acetate |
| 11 | Methyl tert-butyl ether |
| 12 | Tetrahydrofuran |
| 13 | 2-Methyltetrahydrofuran |
| 14 | Toluene |
| 15 | n-Heptane |
| 16 | Cyclohexane |
| 17 | 1,4-Dioxane |
| 18 | Water |
| 19 | Methanol-water (1:1) |
| 20 | Methanol-water (3:1) |
| 21 | Ethanol-water (1:1) |
| 22 | Ethanol-water (3:1)* |
| 23 | Acetonitrile-water (1:1) |
| 24 | Acetone-water (1:2) |
| 25 | Isopropanol-water (1:1) |

TABLE 5

Results for the solubility test of the crystal form A of the compound of formula (I)

| No. | Solvent | Solubility (mg/mL) |
|---|---|---|
| 1 | Methanol | <1.9 |
| 2 | Ethanol | <1.9 |
| 3 | Isopropanol | <2.0 |
| 4 | n-Butanol | <2.0 |
| 5 | Acetonitrile | <1.9 |
| 6 | Acetone | <1.9 |
| 7 | Butanone | <2.0 |
| 8 | Methyl isobutyl ketone | <2.0 |
| 9 | Ethyl acetate | <2.0 |
| 10 | Isopropyl acetate | <2.0 |
| 11 | Methyl tert-butyl ether | <2.0 |
| 12 | Tetrahydrofuran | <2.0 |
| 13 | 2-Methyltetrahydrofuran | <2.0 |
| 14 | Toluene | <2.0 |
| 15 | n-Heptane | <2.0 |
| 16 | Cyclohexane | <2.1 |
| 17 | 1,4-Dioxane | <2.1 |
| 18 | Water | 10.2-20.4 |
| 19 | Methanol-water (1:1) | 4.1-5.2 |
| 20 | Methanol-water (3:1) | 2.1-2.6 |
| 21 | Ethanol-water (1:1) | 10.1-20.2 |
| 22 | Ethanol-water (3:1) * | <2.0 |
| 23 | Acetonitrile-water (1:1) | >103.0 |
| 24 | Acetone-water (1:2) | 20.5-34.2 |
| 25 | Isopropanol-water (1:1) | 6.8-10.2 |

* The suspension of the crystal form A of the compound of formula (I) in ethanol-water (volume ratio 3:1) was dissolved and turned into a clear solution after about 15 hours.

Embodiment 6: In Vitro Synergistic Inhibitory Concentration (SIC) Assay Against Chinese Clinical Isolates Experimental Objective:

This experiment was designed to evaluate the inhibitory activity of the compound of formula (I) against the main carbapenemase.

Experimental Method:

The minimum inhibitory concentration (MIC) of the compound of formula (I) against clinically isolated carbapenemase-producing strains was determined by the broth microdilution method.

1. Drug susceptibility test: the MIC of commonly used antibacterial drugs against clinically isolated bacteria was determined by the broth microdilution method according to the antimicrobial susceptibility test method described in the 2016 edition of the U.S. Clinical and Laboratory Standards Institute (CLSI) document.

2. Strains: 8 KPC-2 carbapenemase-producing strains, 8 NDM-1 metalloenzyme-producing strains, 6 OXA carbapenemase-producing strains, and all strains were clinically isolated *Klebsiella pneumoniae*.

3. Concentration: concentration of the antibacterial drugs: 0.06 μg/mL-128 μg/mL, 12 concentrations in total; the concentration of enzyme inhibitor was fixed at 4 g/mL.

4. Quality control strains: the quality control strains for the drug susceptibility test included *Escherichia coli* ATCC 25922 and ATCC 35218.

Experimental Results:

TABLE 6

Test results of inhibitory activity of the compounds against Chinese clinical isolates

| Bacteria (strain) | Antibacterial agent | Criteria Sensitive | Criteria Drug resistance | MIC range | $MIC_{50}$ | $MIC_{90}$ | drug resistance rate | sensitive rate |
|---|---|---|---|---|---|---|---|---|
| KPC-2 carbapenemase-producing *Klebsiella Pneumoniae* (8 strains) | Meropenem | S <= 1 | R >= 4 | 16-128 | 64 | 128 | 100 | 0 |
| | Ceftazidime | S <= 4 | R >= 16 | 64-128 | >128 | >128 | 100 | 0 |
| | Aztreonam | S <= 4 | R >= 16 | >128 | >128 | >128 | 100 | 0 |
| | Meropenem + the compound of formula (I) | S <= 1 | R >= 4 | <=0.06-0.125 | <=0.06 | 0.125 | 0 | 100 |
| | Meropenem + avibactam | S <= 1 | R >= 4 | <=0.06-0.25 | 0.125 | 0.25 | 0 | 100 |
| | Ceftazidime + the compound of formula (I) | S <= 4 | R >= 16 | <=0.06 | <=0.06 | 0.06 | 0 | 100 |
| | Ceftazidime + avibactam | S <= 4 | R >= 16 | <=0.06-4 | 2 | 4 | 0 | 100 |
| | Aztreonam + the compound of formula (I) | S <= 4 | R >= 16 | <=0.06-1 | <=0.06 | 1 | 0 | 100 |
| | Aztreonam + avibactam | S <= 4 | R >= 16 | <=0.06-8 | 1 | 8 | 0 | 87.5 |
| NDM-1 carbapenemase-producing *Klebsiella Pneumoniae* (8 strains) | Meropenem | S <= 1 | R >= 4 | 2-32 | 4 | 32 | 75 | 0 |
| | Ceftazidime | S <= 4 | R >= 16 | >128 | >128 | >128 | 100 | 0 |
| | Aztreonam | S <= 4 | R >= 16 | 0.5-128 | 64 | >128 | 100 | 0 |
| | Meropenem + the compound of formula (I) | S <= 1 | R >= 4 | <-0.06-2 | <-0.06 | 2 | 0 | 87.5 |
| | Meropenem + avibactam | S <= 1 | R >= 4 | 2-16 | 2 | 16 | 50 | 0 |
| | Ceftazidime + the compound of formula (I) | S <= 4 | R >= 16 | <=0.06-16 | 0.125 | 16 | 12.5 | 87.5 |
| | Ceftazidime + avibactam | S <= 4 | R >= 16 | >128 | >128 | >128 | 100 | 0 |
| | Aztreonam + the compound of formula (I) | S <= 4 | R >= 16 | <=0.06 | <=0.06 | <=0.06 | 0 | 100 |
| | Aztreonam + Avibactam | S <= 4 | R >= 16 | <=0.06-1 | 0.125 | 1 | 0 | 100 |
| OXA-181 carbapenemase-producing *Klebsiella Pneumoniae* (7 strains) | Meropenem | S <= 1 | R >= 4 | 0.5-2 | 0.5 | 2 | 0 | 85.7 |
| | Ceftazidime | S <= 4 | R >= 16 | 128->128 | >128 | >128 | 100 | 0 |
| | Aztreonam | S <= 4 | R >= 16 | >128 | >128 | >128 | 100 | 0 |
| | Meropenem + the compound of formula (I) | S <= 1 | R >= 4 | <=0.06 | <=0.06 | <=0.06 | 0 | 100 |
| | Meropenem + avibactam | S <= 1 | R >= 4 | <=0.06 | <=0.06 | <=0.06 | 0 | 100 |
| | Ceftazidime + the compound of formula (I) | S <= 4 | R >= 16 | <=0.06 | <=0.06 | <=0.06 | 0 | 100 |
| | Ceftazidime + avibactam | S <= 4 | R >= 16 | <=0.06-1 | 1 | 1 | 0 | 100 |
| | Aztreonam + the compound of formula (I) | S <= 4 | R >= 16 | <=0.06 | <=0.06 | <=0.06 | 0 | 100 |
| | Aztreonam + avibactam | S <= 4 | R >= 16 | 0.125-0.5 | 0.125 | 0.5 | 0 | 100 |

Conclusion:

The combination of the compound of formula (I) and an antibiotic exhibited strong antibacterial activity against clinically isolated KPC-2, NDM-1 or OXA-181 type carbapenemase-producing *Klebsiella pneumoniae*. Especially for NDM-1 type carbapenemase-producing bacteria, the inhibitory activity of the compound (1) was significantly better than that of avibactam.

The lungs were ground with an IKA T10 homogenizer (the maximum speed was 20S, repeated once). The homogenate was diluted in a gradient manner and spotted on a tryptone soy agar plate. The plate was placed in a 37° C. incubator for bacterial incubation. After 24 hours, the plate was taken out and the number of single colonies grown in each homogenate with a gradient dilution on the plate was counted, and the amount of bacterial load in the lung of each mouse was calculated.

Experimental Scheme:

TABLE 7

Efficacy evaluation of the compound of formula (I) and reference compound OP-0595 in mouse thigh muscle infection model

| Group | Class of strains | Dose | Administration route | Experimental procedure | Number of mice |
|---|---|---|---|---|---|
| 1 | *Klebsiella pneumoniae* (ATCC BAA-1705, KPC-2) | Normal saline | Intraperitoneal injection (ip) | After bacterial infection, the first dose was administered after 2 hours, the second dose was administered at the 10th hour, and the amount of bacterial load in the lung of each group of mice was checked at the 24th hour. | 4 |
| 2 | | Ceftazidime (50 mpk) | | | 5 |
| 3 | | Ceftazidime (25 mpk) & avibactam (001) (6.25 mpk) | | | 5 |
| 4 | | Ceftazidime (25 mpk) & OP-0595 (088) (6.25 mpk) | | | 5 |
|   | | Ceftazidime (25 mpk) & the compound of formula (I) (189) (6.25 mpk) | | | 5 |
|   | | Ceftazidime (50 mpk) & avibactam (001) (12.5 mpk) | | | 5 |
| 5 | | Ceftazidime (50 mpk) & OP-0595 (088) (12.5 mpk) | | | 5 |
| 6 | | Ceftazidime (50 mpk) & the compound of formula (I) (12.5 mpk) | | | 5 |

Embodiment 7: Mouse Lung Infection Model

Experimental Objective:

This experiment was designed to determine whether the compound of formula (I) has pharmacological effects in a mouse lung infection model and further evaluate whether the compound of formula (I) has a significant advantage over the reference compound OP-0595 on pharmacological effect.

Experimental Materials:

Female CD-1 mice of about 7 weeks old, weighing 26-28 g; cyclophosphamide was injected at a dose of 150 mg/kg 4 days before infection, and further 100 mg/kg 1 day before infection; the bacteria for infection was *Klebsiella pneumoniae* (ATCC BAA-1705, KPC-2). The compound of formula (I) and the reference compound OP-0595 were synthesized in the laboratory.

Experimental Procedure:

Female CD-1 mice were infected with *Klebsiella pneumoniae* by intranasal instillation. Each mouse was instilled with 50 μL of bacterial liquid through nasal cavity at a dose of 3.14E+07 CFU per mouse. At 2 h, 4 h, 6 h and 8 h after infection, each group of mice were treated with a corresponding compound or a combination of compounds by intraperitoneal injection.

At 10 h after infection, the mice in groups 1, 2 and 3 were euthanized, and the lungs were taken out and placed in 50 mL centrifuge tubes containing 10 mL of sterile normal saline, the tubes were placed on wet ice and transferred to BSL-2 laboratory for CFU counting. At 20 h after infection, the mice in groups 4, 5 and 6 were euthanized and treated according to the same procedure.

Figure 5:
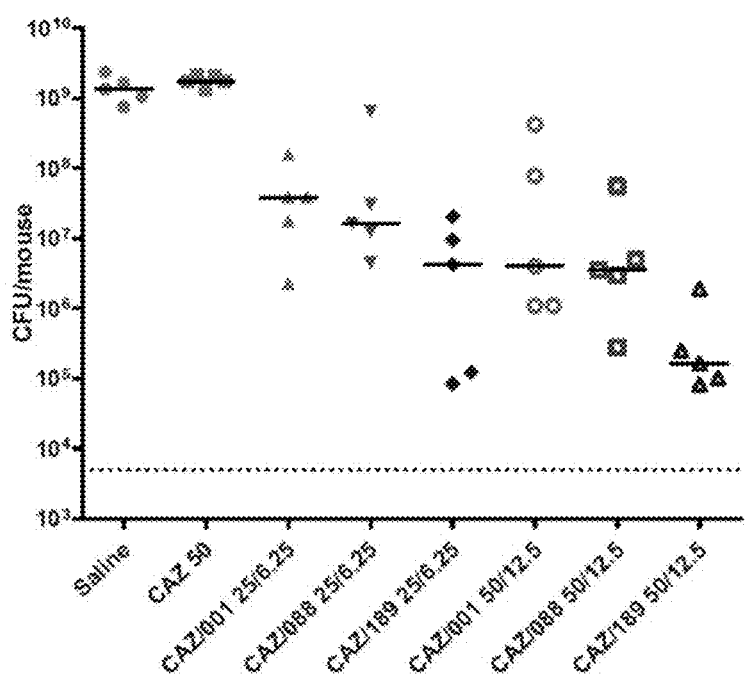
FIG. 5 shows the test results of the compound of formula (I) on KPC type β-lactamase producing *Klebsiella pneumoniae*.

Experimental Results:

According to the experimental scheme in Table 7, the pharmacological effect results are shown in FIG. 5. It can be seen from the figure of pharmacological effect results that the amount of bacterial load in the group of the compound of formula (I) in the mouse model was reduced by 0.5-1.5 logs than that in the reference group of compound OP-0595 at two different doses. The compound of formula (I) is significantly more potent than the reference compound OP-0595.

The in vitro bacterial inhibition experiment, in vitro enzyme inhibition experiment, and in vivo pharmacological effect experiment evaluated the embodiment from different aspects. The compound of formula (I) in the embodiment shows significant advantages over the reference compound OP-0595. In the current situation where new clinical drugs are urgently needed to combat the increasingly serious drug-resistant bacterial infections, the compound in the embodiment is a class of drugs with great potential to solve this problem. It can be predicted that compared with the currently preferred reference compound OP-0595, the compound of formula (I) can show a better clinical effect in the future clinical application.

What is claimed is:

1. A crystal form A of the compound of formula (I), wherein the X-ray powder diffraction pattern thereof comprises characteristic diffraction peaks at the following angle 2θ: 16.053±0.2°, 16.53±0.2°, 22.782±0.2° and 25.742±0.2°,

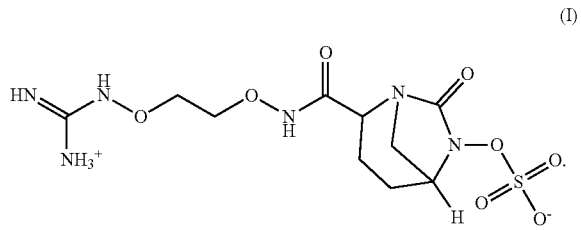 [SMILES: N=C([NH3+])NOCCONC(=O)C1CCC2CN1C(=O)N2OS(=O)(=O)[O-]]

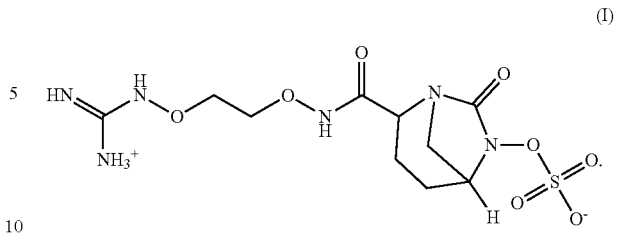

2. The crystal form A of the compound of formula (I) as defined in claim 1, wherein the X-ray powder diffraction pattern thereof comprises characteristic diffraction peaks at the following angle 2θ: 16.053±0.2°, 16.53±0.2°, 18.501±0.2°, 21.302±0.2°, 21.778±0.2°, 22.782±0.2°, 25.742±0.2° and 27.833±0.2°.

3. The crystal form A of the compound of formula (I) as defined in claim 2, wherein the XRPD pattern thereof is as shown in FIG. 1.

4. The crystal form A of the compound of formula (I) as defined in claim 1, wherein the differential scanning calorimetry curve thereof has an exothermic peak at 221.11±3° C.

Figure 2:
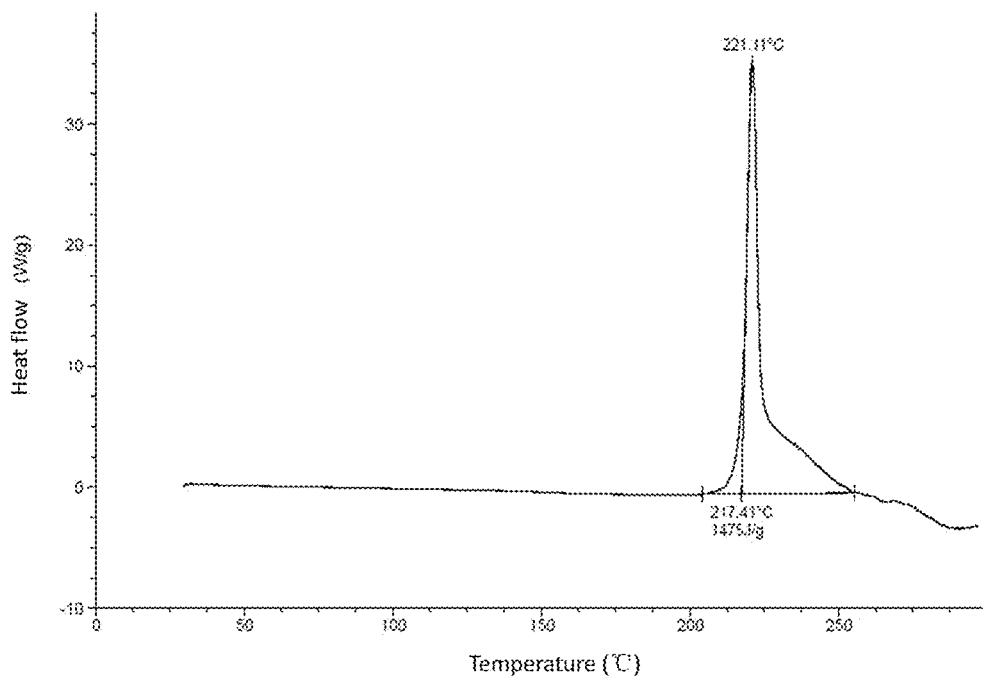
FIG. 2 is the DSC pattern of the crystal form A of the compound of formula (I).

5. The crystal form A of the compound of formula (I) as defined in claim 4, wherein the DSC pattern thereof is as shown in FIG. 2.

6. The crystal form A of the compound of formula (I) as defined in claim 1, wherein the thermogravimetric analysis curve thereof has a weight loss of 0.5689% occurred at 194.61±3° C.

Figure 3:
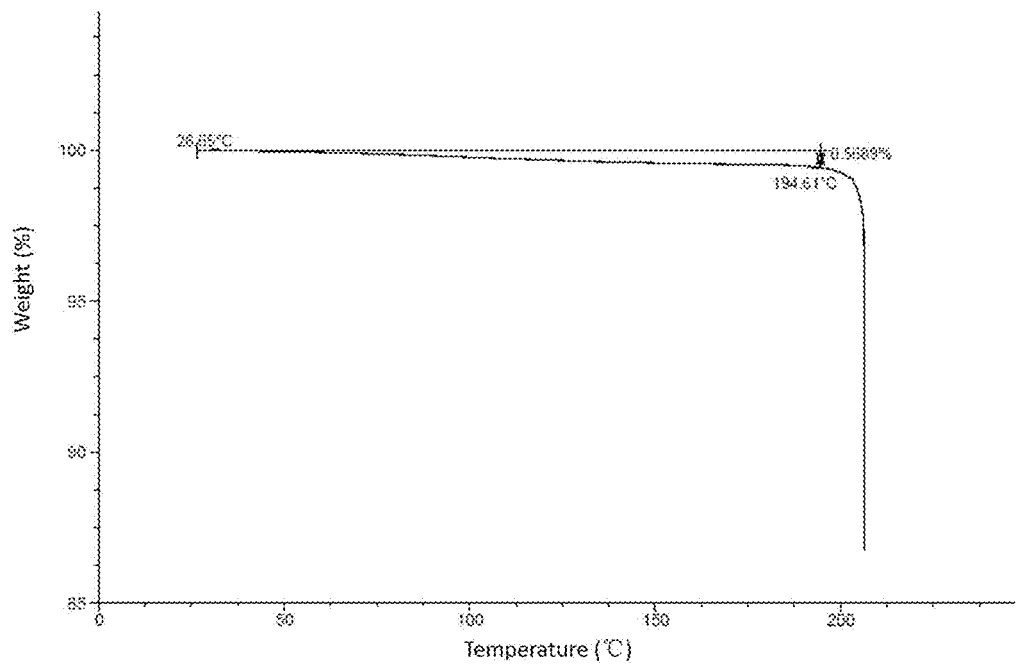
FIG. 3 is the TGA pattern of the crystal form A of the compound of formula (I).

7. The crystal form A of the compound of formula (I) as defined in claim 6, wherein the TGA pattern thereof is as shown in FIG. 3.

8. A method for preparing a crystal form A of the compound of formula (I), comprising:
(a) adding the compound of formula (I) to a solvent and heating to 55-60° C. until it is completely dissolved;
(b) slowly cooling to 0° C. under stirring;
(c) stirring for 10-16 hours for crystallization;
(d) filtering, and drying by suction;
wherein the solvent is pure water;

9. A method for treating bacterial infection in a subject in need thereof, comprising administering an effective amount of the crystal form A of the compound of formula (I) as defined in claim 1 as a β-lactamase inhibitor to the subject.

10. The method for treating bacterial infection in a subject in need thereof as defined in claim 9, wherein the bacterial infection is infection of carbapenemase-producing bacteria.

11. The method for treating bacterial infection in a subject in need thereof as defined in claim 9, wherein the bacterial infection is infection of KPC-2 carbapenemase-producing *Klebsiella pneumoniae*, NDM-1 carbapenemase-producing *Klebsiella pneumoniae*, or OXA-181 carbapenemase-producing *Klebsiella pneumoniae*.

12. A method for treating bacterial infection in a subject in need thereof, comprising administering an effective amount of the crystal form A of the compound of formula (I) prepared by the method as defined in claim 8 as a β-lactamase inhibitor to the subject.

13. The method for treating bacterial infection in a subject in need thereof as defined in claim 12, wherein the bacterial infection is infection of carbapenemase-producing bacteria.

14. The method for treating bacterial infection in a subject in need thereof as defined in claim 12, wherein the bacterial infection is infection of KPC-2 carbapenemase-producing *Klebsiella pneumoniae*, NDM-1 carbapenemase-producing *Klebsiella pneumoniae*, or OXA-181 carbapenemase-producing *Klebsiella pneumoniae*.

Figure 4:
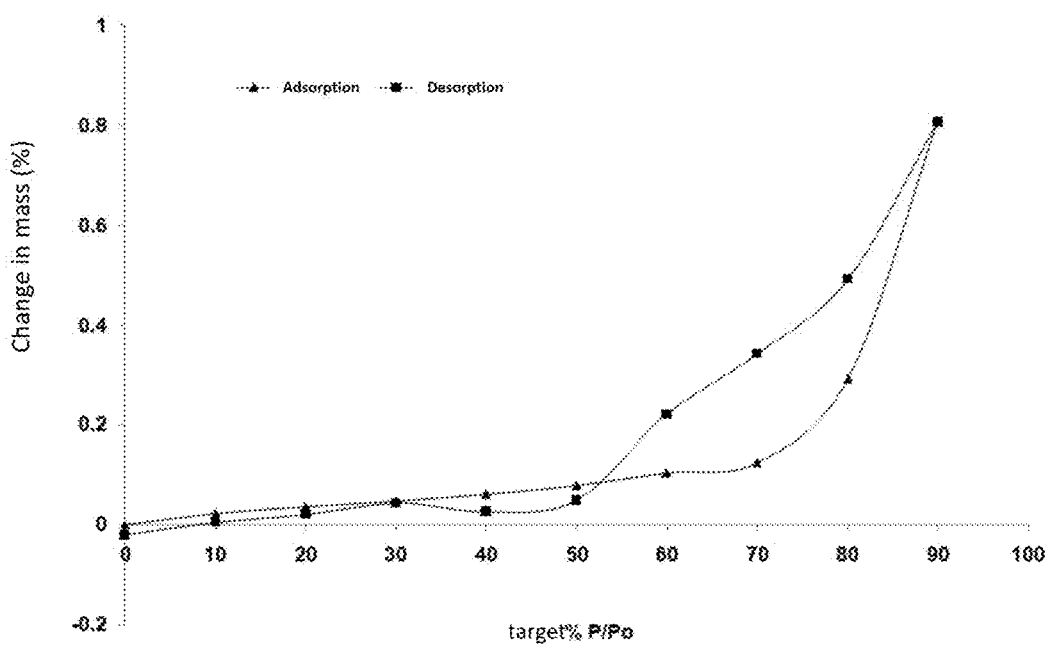
FIG. 4 is the DVS pattern of the crystal form A of the compound of formula (I).

15. The crystal form A of the compound of formula (I) as defined in claim 1, wherein the DVS pattern thereof is as shown in FIG. 4.

16. The crystal form A of the compound of formula (I) as defined in claim 1, wherein the crystal form A of the compound of formula (I) has a hygroscopic weight gain of 0.2910% at 25° C./80% RH.

* * * * *